United States Patent

Maxwell

[11] 4,092,849
[45] June 6, 1978

[54] METHOD AND APPARATUS FOR MEASURING MELT ELASTICITY OF POLYMERS

[76] Inventor: Bryce Maxwell, 19 McCosh Cir., Princeton, N.J. 08540

[21] Appl. No.: 801,189

[22] Filed: May 27, 1977

[51] Int. Cl.² .............................................. G01N 3/24
[52] U.S. Cl. .................................................... 73/101
[58] Field of Search ...................... 73/101, 99, 15.6, 60

[56] References Cited

U.S. PATENT DOCUMENTS

| | | | |
|---|---|---|---|
| 3,277,700 | 10/1966 | Myerholtz | 73/99 |
| 3,479,858 | 11/1969 | Umeno et al. | 73/99 |
| 3,680,366 | 8/1972 | Moser et al. | 73/99 |

*Primary Examiner*—Anthony V. Ciarlante
*Attorney, Agent, or Firm*—Albert Sperry; Frederick A. Zoda; John J. Kane

[57] ABSTRACT

An apparatus and method for measuring the elastic properties of polymer melts and polymer solutions including the placement of a specimen of the material to be tested, within the intervening space between two members both of which are capable of low friction rotation about a common axis, further including a drive apparatus to forcibly rotate one member about the axis to shear the specimen, also including the measuring of the force required to shear the specimen, in order to determine the modulus of elasticity, yield stress and steady state viscosity of the specimen, further releasing the member not forcibly rotated and measuring the recoverable strain and rate of strain recovery by measuring the motion of the released member as a function of time for the purposes of determining the elastic characteristics of the specimen, further including a light source directed along the axis of rotation of the members into an optical fiber along the center line thereof so shaped to emerge in a direction parallel to the axis of rotation but at a point distant therefrom, the light source being adapted to be turned off and on as a fucntion of time in a predetermined manner such that a photograph of the end of the optical fiber distant from the axis of rotation determines the position of the released member as a function of time thereby measuring the rate of strain recovery and the total amount of strain recovery of the specimen.

17 Claims, 3 Drawing Figures

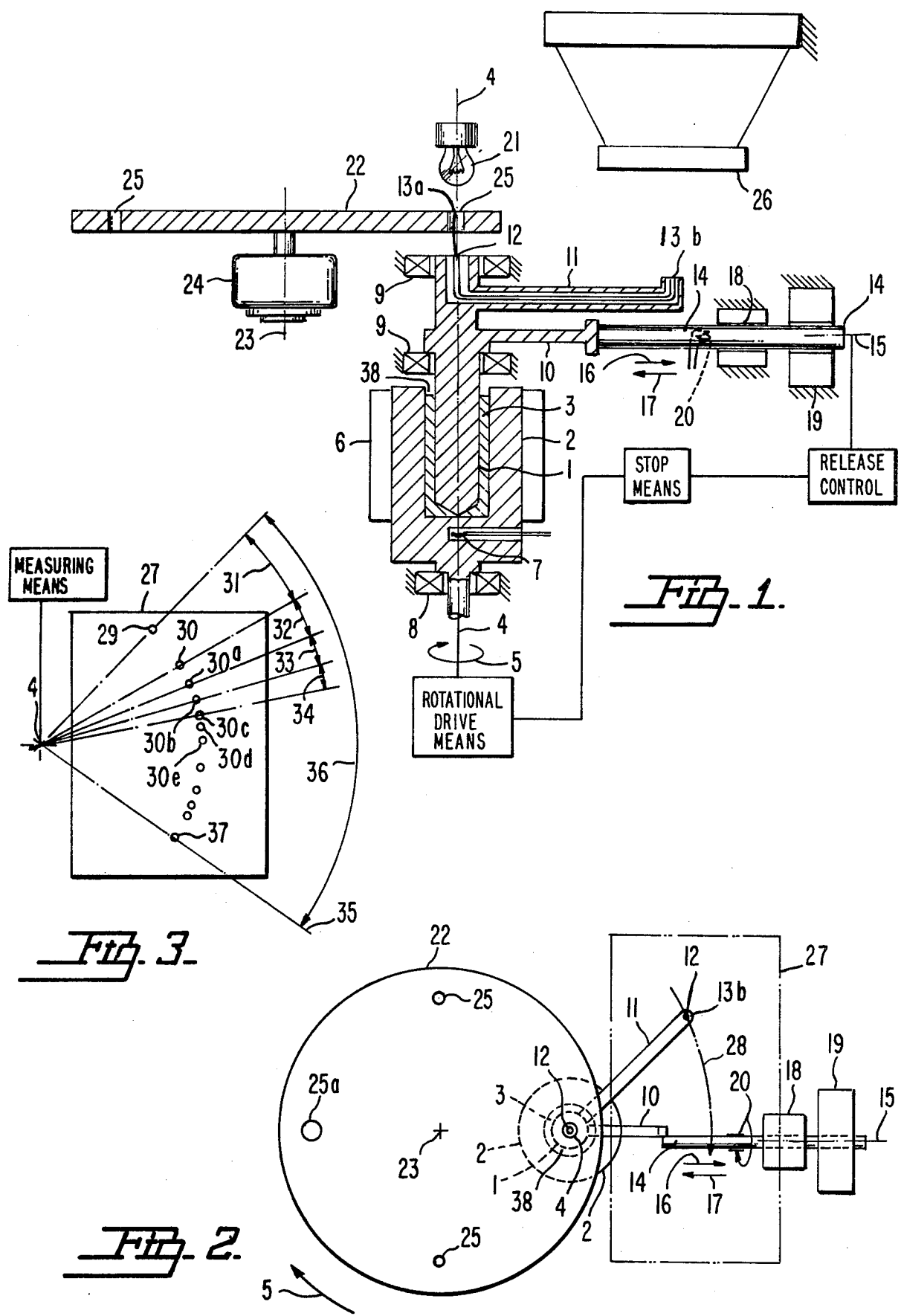

METHOD AND APPARATUS FOR MEASURING MELT ELASTICITY OF POLYMERS

BACKGROUND OF THE INVENTION

1. Field of the Invention

In the processing of polymer materials the material to be processed is put into a fluid state either by the application of heat or by dissolving it in a low molecular weight solvent to form a solution. The resulting fluid is of a viscoelastic nature and may be formed into a fabricated shape either by flow under the force of gravity or by flow under an externally applied pressure.

In order to properly design such processing operations and the equipment associated therewith it is important to have measurements of the rheological behavior of the viscoelastic polymer melt or solution. Since these materials are viscoelastic, it is important and necessary to measure both the viscous and elastic behavior of the material.

There are well established methods of measuring the viscous properties, for example the standard melt index test (American Society for Testing and Materials, D-1238). Methods of measuring the elastic properties are not as well established and no satisfactory method is as yet available. The present invention is intended to fill this need.

2. Description of the Prior Art

Current methods of measuring the elastic properties of polymer melts and solutions include: (1) The Orthogonal Rheometer as first disclosed by Bryce Maxwell and Richard P. Chartoff in Transactions of the Society of Rheology 9:1, 41-52 (1965). This method measures the dynamic elastic modulus but cannot measure the elastic recoverable strain, (2) The well known Couette apparatus and the Searle apparatus (see for example, Rheology Vol. 3 pg. 29, Academic Press, N.Y., N.Y.) Both the Couette and Searle methods involve shearing the material specimen in an annular space between a cylindrical center member and an outer cup member and measuring the force required to achieve the shearing as a function of the rate of shear. The present invention discloses an improvement of this type of apparatus usable to measure the elastic recoverable strain.

Past efforts in devising apparatus for the measurement of recoverable strain have resulted in complex and expensive systems both in the apparatus and in the reduction of the data generated. For example Maxwell and McCord (Modern Plastics Magazine, Sept. 1961) resorted to a system involving a motion picture camera photographing the motion of a lever attached to the central cylindrical member simultaneously with a stop watch to record the strain recovery as a function of time. Such a system is complex in the apparatus required and time consumed in the delay required to develop the motion picture film and also tedious in the frame by frame analysis of photographic recording.

The present invention overcomes many of these undesirable features due to the simple manner in which the data is immediately available.

SUMMARY OF THE INVENTION

The present invention includes a specimen holding space located between two coaxially rotatable members, rotating one member to accomplish shearing of the specimen, stopping the shearing and concurrently releasing the other member, following the rotation of the released member as a function of time to measure the rate of strain recovery and the total amount of recoverable strain. The measurement of the position of the released member as a function of time may be accomplished by shining an intermittent light source at a predetermined frequency on one end of a light transmitting optical fiber which is located along the axis of rotation of the members. The other end of the optical fiber, which is located at a distance from the axis of rotation and oriented parallel with respect to the axis of rotation, may be photographed in a time exposure still camera to provide a record of the position of the released member in the form of points of light on the photograph. These points of light are known with respect to time by the predetermined blinking frequency of the intermittent light source.

It should be noted that although the apparatus and method of the present invention has been found to be advantageous in the measurement of the rheological prooperties of polymer melts and solutions it also is applicable to measuring the properties of other materials such as food products, for example bread dough, mayonnaise, etc. or biological materials, for example blood, synovial fluid, etc.

It is an object of the present invention to provide an improved method and apparatus for measuring the elastic properties of polymer melts and solutions which is relatively uncomplicated, lends itself to ease of manufacture, and is simple to operate or maintain.

It is a further objective of the present invention to provide a method and apparatus for the measurement of recoverable strain in polymer melts and polymer solutions that provides the data of interest essentially immediately after completion of the measurement.

It is a further objective of the present invention to provide a method and apparatus for the measurement of the rate of strain recovery in polymer melts and polymer solutions that provides the data of interest essentially immediately after the completion of the measurement.

It is a major objective of the present invention to provide a method and apparatus to measure the recoverable strain and recoverable strain rate in polymeric melts and solutions which method and apparatus solve at least some of the problems confronting this field of technology.

BRIEF DESCRIPTION OF THE DRAWINGS

While the invention is particularly pointed out and distinctly claimed in a concluding part of the specification, preferred embodiments are set forth in the following detailed description which may best be understood when read in connection with the accompanying drawings, in which:

FIG 1 is an axial sectional view of a preferred embodiment of the present invention;

FIG. 2 is a plan view of the embodiment shown in FIG. 1; and

FIG. 3 shows a typical photographic data record obtained when utilizing the preferred embodiment of the present invention to measure the recoverable strain of the specimen.

DETAILED DESCRIPTION OF THE PREFERRED EMBODIMENT

As shown in FIG. 1, an essentially cylindrical member 1 is centrally located within the cylindrical hollow bore of a second member 2 to provide an intervening space 38, which is essentially annular, therebetween to hold the specimen 3 to be tested. Conventional drive means is provided to rotate member 2 about axis of rotation 4 as indicated by arrow 5. Conventional heating means such as electric resistance heater 6 is provided together with a temperature controling or measuring device such as a thermocouple 7 to bring the specimen 3 to the desired test temperature. Member 2 is mounted in low friction bearing 8.

Member 1 is mounted in low friction bearings 9 so that it can rotate about axis 4. A releasable restraining means such as a restraining arm 10 is mounted as an integral part of member 1. In addition a tube 11 is also mounted as an integral part of member 1. An optical fiber 12, such as an assembly of glass fibers, is mounted in a manner such that its first end 13(a) is along the axis of rotation 4 and its second end 13(b) is axially positioned at a distance from the axis of rotation 4 and parallel with respect thereto.

A beam member 14 is provided to selectively prevent rotation of member 1 through contact with the restraining arm 10. Said beam member is operably capable of being moved along its axis 15 in accordance with arrow 16 to an outer position and arrow 17 to an inner position in a manner such as to prevent rotation of arm member 10 or to release member 10 thereby permitting rotation of member 1 about axis 4. Member 14 may be moved along axis 15 in a slide bearing member 18 by means of an electromagnetic means 19 or other suitable means.

In addition a force measuring element such as a strain gauge stress transducer 20 may be attached to element 14 to measure the force exerted by arm 10 on beam 14 during the shearing part of the experimental cycle. Transducer 20 may be of any nature commonly available in the instrumentation field.

In addition a light source 21 is provided. Said light source 21 is directed co-axially with axis of rotation 4 and unless interrupted shines on the first end 13(a) of optical fiber 12. In order to interrupt or turn on and off the illumination from light source 21, a light interrupting means such as an opaque disk 22 is provided. Disk 22 is mounted on axis of rotation 23 and rotated at a predetermined rotational speed by motor 24. Apertures or holes 25 are provided in disk 22 at intervals such that when an aperture 25 is in a position corresponding to axis of rotation 4 the radiation from light source 21 passes through disk 22 and impinges on optical fiber 12. When the holes 25 are not in a position corresponding to axis of rotation 4 the radiation from light source 21 is prevented from impinging on optical fiber 12 by the opaque disk 22.

A time exposure still picture camera 26 may provide a recording means to photograph the light emitting from end 13(b) of the optical fiber 12.

FIG. 2 is a plan view of the preferred embodiment of the present invention in which the parts described above are identified and numbered in accordance with FIG. 1. Reference numeral 27 outlines the field of view or picture taken by camera 26. Also reference numeral 28 identifies an example of the path of travel of the second end 13(b) of the optical fiber 12 upon release.

FIG. 3 shows an example of a typical photographic record of the recoverable strain of the specimen in which the parts described are identified in accordance with the reference numerals in FIG. 1 and FIG. 2. Picture 27 includes an initial postion photographic image 29 illustrating the start position of strain recovery. Image 30 and 30(a) through 30(e) indicate the location of end 13(b) of optical fiber 12 as each hole 25 becomes vertically collimated with light source 21. The arcuate distances 31, 32, 33, 34 are measurements of the angles of recovery of member 1 corresponding to the time elapsed inbetween the intermittent bursts of light which cast images 29, 30, 30(a), 30(b), 30(c), 30(d) and 30(e) upon picture 27. Angular position 35 illustrates the end point for the total angular movement of the member 1. Arcuate distance 36 is the total angular distance of movement between the initial position and the final angular position 35. Image 37 represents the final image cast by the intermittent light source when the member 1 comes to rest.

In some cases the rate of strain recovery is initially very rapid and then very slow. For the very rapid strain recovery range a large number of apertures 25 in disk 22 are needed in order to interrupt the light beam at very short intervals of time to accurately record the rapid recovery as a function of time. On the other hand when the recovery is slow it is desirable to identify the position of the outer end of tube 11 at longer intervals of time. This can be accomplished by making one of holes 25 larger than the others such as enlarged hole 25(a) thereby increasing the light intensity transmitted through this hole and thereby producing a brighter spot of light on the photograph once per rotation of disk 22. These intermittent bright spots will serve to identify the position of recovery of strain at these longer intervals of time where the more rapid intervals of light exposure produced by the other smaller holes may become blurred by overlapping.

The procedure of measurement includes insertion of a specimen 3 of material to be tested for elastic properties in the annular space 38 to be brought to the desired test temperature by heating of member 2 through control in any conventional manner in conjunction with heating means 6 and thermocouple 7. When temperature equilibrium has been established a drive means operating along arrow 5 is started to rotate member 2 while member 1 is restrained from rotation by beam 14 being in abutment with arm 10 thereby causing specimen 3 to be sheared. During this shearing the force required to accomplish the shearing may be measured by the transducer 20 and may be recorded by any conventional means.

When the desired amount of shearing has taken place the drive means may be stopped by any means such as a limit switch or other conventional means and the rotation of member 2 will be similarly stopped such as by a cam associated with member 2 that hits an immovable object. Concurrent with or prior to the cessation of shearing, light 21 is actuated and drive 24 is turned on to rotate disk 22. Light from source 21 radiating through holes 25 and then traversing from end 13(a) to end 13(b) through the optical fiber 12 is observed by the camera 26 to produce the initial image 29 on the photograph 27 to establish the point of start of the strain recovery.

Concurrently with the cessation of shearing the electromagnet 19 is activated by any conventional means such as a switch associated with the method of stopping the shearing. The activation of the electromagnet 19 causes the beam 14 to move in the direction 16 thereby releasing the restraining arm 10 and allowing the stored elastic strain in the specimen 3 to cause the member 1 to move in the indicated direction at a rate and magnitude directly related to the rate of recovery of strain and the magnitude of the recoverable strain stored in the specimen 3 as a result of the previous shearing imparted by drive 5.

As the strain recovery takes place during a period of time the light 21 is "chopped" by the disk 22 and the associated apertures 25 in a fashion related to the rotational speed of drive 24 and the number of holes 25 in disk 22 thereby establishing the frequency at which the end 13(b) of the optical fiber "blinks" and thereby determining the location of the points of light 30(a), 30(b), 30(c) recorded on the photograph 27 both as to time and position.

As a result of the record on the still photograph 27 of the motion of end 13(b) of the optical fiber 12, it is a simple matter to measure the angles 31, 32, 33, 34 etc. to obtain a measure of the rate of recovery of stored elastic strain as a function of time and to measure the total recoverable strain by measuring the total arcuate distance 36 by any conventional angle measuring instrument such as a protractor.

It can therefore be seen that the elastic, recoverable strain properties of materials can be measured by this improved method and apparatus as disclosed herein which is uncomplicated and provides ease of manufacture, maintenance and operation, in addition, to providing the recorded data essentially immediately after completion of the test experiment, especially when a self-developing camera system, is employed.

There are, of course, other methods of measuring the motion of member 1 as a function of time. One could attach a variable resistance potentiometer, a variable transmission optical wedge or a variable capacitance capacitor to member 1 and provide the output therefrom to any high-speed conventional recorder. But this would increases the complexity of the apparatus and would require the use of a high-speed recorder and thereby incur considerable expense. However, the present invention can measure recoverable strain rates that are unlimited as to their speed by simply providing as many holes 25 and as high a rotational speed of drive 24 as are needed to produce a photographic recording 27 from which the desired strain recovery data may be resolved.

It should be noted that other optical methods of recording the recoverable strain have and could be employed, such as a system of mirrors reflecting a light beam off of a surface on an element such as 1 in a radial direction perpendicular to axis 4. Such methods are of increased complexity since the recording of the position of element 1 would have to be made along a circular arc radially positioned about axis 4 thereby requiring special, unconventional photographic equipment, in comparison to that used in the present invention which simply requires a flat plate, time exposure, conventional camera.

It should be noted that the principle of recording the recoverable strain in the apparatus of the present invention is free of friction, an essential factor in the accuracy of the measurement. It is also low in inertia, an important consideration in the accuracy of the initial part of the recovery curve.

It should also be noted that principle features of the strain recovery apparatus of the present invention include, firstly, the incident light beam is aimed directly along the axis of rotation of the recovering member, thereby introducing the chopped light into the optical fiber regardless of what angular position of recovery it is in. Secondly, the other end of the optical fiber, to be photographed, is aimed along an axis parallel to the axis of rotation of the recovering member to provide motion always in a plain that is the focal plain of the camera. Other optical systems previously used do not have this simplifying feature and require more elaborate, expensive, complex optical systems.

In order to facilitate the accurate determining of the distances between individual spots on the photographic record a measuring means may be incuded as shown in FIG. 3 in order to determine the exact absolute measurement or angular measurement therebetween. Also in order to assure simultaneity of the actuation of the release control with the cessation of operation of the rotational drive means a stop means may be included as shown in FIG. 1. The stop means will thus insure that the proper timing is maintained between the releasing by the release control means and the control of the rotational drive means.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention. For example, numbers 1 and 2 may be replaced by other coaxially rotating geometries such as a cone and a plate or two disks with surfaces perpendicular to the axis of rotation 4 or other similar shearing geometries. As such the matter covered in the following claims includes all such modifications and changes as may fall within the entire true spirit and scope of the present invention.

I claim:

1. An apparatus for measuring elastic properties of polymers comprising:
   (a) a first member mounted for low friction rotation, said first member defining an axis of rotation;
   (b) a second member mounted for low friction rotation about said axis of rotation and positioned adjacent said first member to define therebetween an intervening space to receive therein a specimen of polymer to be tested;
   (c) means to rotationally drive said first member about said axis of rotation to allow relative rotational movement between said first member and said second member to cause shearing of the specimen positioned therebetween in said intervening space;
   (d) releasable retaining means to selectively prevent rotation of said second member;
   (e) stop means to selectively halt operation of said rotational drive means and to stop rotation of said first member;
   (f) a light source directed along said axis of rotation;
   (g) an optical fiber means within said second member to rotate therewith, said optical fiber means including a first end oriented along said axis of rotation and a second end distant from said axis of rotation and parallel with respect thereto, said optical fiber means adapted to transmit light from said first end to said second end;
   (h) light interrupting means located in the light flow path between said light source and said first end of said optical fiber means to intermittently block at a known frequency the light from said light source from entering said first end of said optical fiber means; and
   (i) recording means for recording the movement of said second end of said optical fiber means and, hence, the rotation of said second member by recording the light emitted from said second end of said optical fiber means.

2. The apparatus as defined in claim 1 wherein said first member is of a hollow cup-like substantially cylindrical configuration and said second member is of a substantially cylindrical configuration positioned within the cup-like configuration of said first member to define said intervening space therebetween to be annular.

3. The apparatus as defined in claim 1 wherein said recording means comprises a photographing means for photographing the motion of said second end of said optical fiber to record the strain recovery of the specimen as a function of time.

4. The apparatus as defined in claim 1 further comprising a temperature control means to maintain the temperature of the specimen within predetermined desirable limits.

5. The apparatus as defined in claim 1 wherein said light interrupting means comprises a rotatable opaque disk which defines a plurality of apertures therein to intermittently prevent light from entering said optical fiber means upon rotation thereof.

6. The apparatus as defined in claim 5 wherein said apertures are of different cross-sectional areas to provide light output to said recording means at differing intensities.

7. The apparatus as defined in claim 1 wherein said releasable retaining means comprises a laterally movable beam movable between an inner position closer to said second member and an outer position farther from said second member, said second member also including an outwardly projecting arm affixed thereto being adapted to engage said beam when in the inner position, and to disengage from said beam when in the outer position to allow rotation of said second member.

8. The apparatus as defined in claim 1 further including a means for measuring the movement of said second member as recorded by said recording means to determine the elastic properties of the specimen.

9. An apparatus for measuring elastic properties of polymers comprising:
(a) a first member of hollow cup-like substantially cylindrical configuration being mounted for low-friction rotation, said first member defining an axis of rotation;
(b) a second member positioned within the cup-like configuration of said first member to define therebetween an intervening annular space to receive a specimen to be tested therein, said second member being mounted for low-friction rotation about said axis of rotation;
(c) means to rotationally drive said first member about said axis of rotation to allow relative rotational movement between said first member and said second member to cause shearing of the specimen positioned therebetween in said intervening space;
(d) releasable retaining means to selectively prevent rotation of said second member;
(e) stop means to selectively halt operation of said rotational drive means and to stop rotation of said first member;
(f) a light source directed along said axis of rotation;
(g) an optical fiber means within said second member to rotate therewith, said optical fiber means including a first end oriented along said axis of rotation and a second end distant from said axis of rotation and parallel with respect thereto, said optical fiber means adapted to transmit light from said first end to said second end;
(h) light interrupting means located in the light flow path between said light source and said first end of said optical fiber means to intermittently block in a known frequency the light from said light source from entering said first end of said optical fiber means, said light interrupting means including a rotatable disk which defines a plurality of apertures therein;
(i) photographing means for recording the movement of said second end of said optical fiber means and, hence, the rotation of said second member by photographing the light emitted from said second end of said optical fiber means to record the rate of strain recovery of the specimen as a function of time; and
(j) temperature control means to maintain the temperature of the specimen within predetermined desirable limits.

10. The apparatus as defined in claim 9 wherein said apertures are of different cross-sectional areas to provide light output to said recording means at differing intensities.

11. The apparatus as defined in claim 9 wherein said rotatable opaque disk defines a disk axis about which said disk is rotatable at a constant rotational speed, said disk axis being parallel to said axis of rotation of said first member and said second member and displaced at a distance therefrom, said apertures in said disk being aligned with said axis of rotation of said first member and said second member to intermittently allow light from said light source at regular intervals to pass through one of said apertures into said first end of said optical fiber means.

12. The apparatus as defined in claim 11 wherein one of said apertures is larger than the other of said apertures to record each full revolution of said disk on said photographing means to facilitate measurement over larger periods of time.

13. A method for measuring the elastic properties of polymer materials comprising:
(a) introducing a specimen of the material to be tested into an intervening space between the opposing surfaces of two co-axially rotatable members;
(b) rotating one member while restraining the rotation of the other member to shear the specimen;
(c) shining light along the axis of rotation of the members onto a first end of an optical fiber, said optical fiber being located along the axis of rotation of the members onto a first end of an optical fiber located along the axis of rotation to allow the light to travel along the optical fiber to a second end positioned distant from the axis of rotation and parallel with respect thereto;
(d) interrupting said light beam as a function of time;
(e) stopping rotation of the rotating member while concurrently releasing the restrained member;
(f) recording the movement of the second end of the optical fiber as a function of time; and
(g) measuring the distances between the recorded positions of the second optical fiber and to determine the rate of strain recovery and the total strain recovery of the specimen.

14. The method as defined in claim 13 wherein said rotating comprises rotating of a cup-like substantially cylindrical external member and wherein said restraining comprises restraining of a substantially cylindrical internal member positioned within the external member.

15. The method as defined in claim 14 wherein said stopping comprises stopping of said rotating of the external member simultaneously with releasing of said restraining of said internal member.

16. The method as defined in claim 13 wherein said interrupting includes placement of an apertured rotatable disk between the source of the light and the first end of the optical fiber.

17. The method as defined in claim 13 wherein said recording comprises photographing the varying positions of the light emitted from the second end of the optical fiber.

* * * * *